(12) United States Patent
Waddell et al.

(10) Patent No.: US 6,485,902 B2
(45) Date of Patent: Nov. 26, 2002

(54) **USE OF BACTERIOPHAGES FOR CONTROL OF *ESCHERICHIA COLI* O157**

(76) Inventors: Thomas E. Waddell, 1795 Brock Road, Freelton Ontario (CA), L0R 1K0; Amanda Mazzocco, 2 Valerlote Place, Guelph Ontario (CA), N1G 3X1; Jennifer Pacan, R.R.#4, Rockwood Ontario (CA), N0B 2K0; Rafig Ahmed, 35 Lake Village Road, Winnipeg Manitoba (CA), R3G 4M8; Roger Johnson, 36 Glasfow Street, North Guelph Ontario (CA), N11I 4V5; Cornelius Poppe, 11 Devonshire Place, Guelph Ontario (CA), N1E 1C5; Rasik Khakhria, 32 Amberwood Crescent, Nepean Ontario (CA), K2E 7B9

(*) Notice: Subject to any disclaimer, the term of this patent is extended or adjusted under 35 U.S.C. 154(b) by 0 days.

(21) Appl. No.: 09/873,949

(22) Filed: Jun. 5, 2001

(65) Prior Publication Data

US 2002/0090356 A1 Jul. 11, 2002

Related U.S. Application Data

(60) Provisional application No. 60/209,608, filed on Jun. 6, 2000.

(51) Int. Cl.$^7$ .............................. C12Q 1/70; A01N 63/00
(52) U.S. Cl. ............................................ 435/5; 424/93.6
(58) Field of Search ................................... 435/5, 93.6

(56) References Cited

U.S. PATENT DOCUMENTS

| | | | |
|---|---|---|---|
| 4,891,210 A | 1/1990 | Norris | 424/50 |
| 4,957,686 A | 9/1990 | Norris | 424/50 |
| 5,688,501 A | 11/1997 | Merril et al. | 424/93.6 |
| 5,766,892 A | 6/1998 | Merril et al. | 424/93.6 |
| 5,811,093 A | 9/1998 | Norris | 424/93.6 |
| 6,121,036 A | 9/2000 | Ghanbari et al. | 435/235.1 |

FOREIGN PATENT DOCUMENTS

| CA | 2023556 | 2/1991 |
|---|---|---|

OTHER PUBLICATIONS

Rafiq Ahmed, Cheryl Bopp, Al Borczyk and Shanti Kasatiya, Apr., 1987, "Phage–Typing Scheme for *Escherichia coli* O157:H7", Journal of Infectious Diseases 155: 806–809.

Indira Kudva, Srdjan Jelacic, Phillip I. Tarr, Philip Youderian and Carolyn J. Hovde, Sep. 1999, "Biocontrol of *Escherichia coli* O157 with O157–Specific Bacteriophages", Applied and Environmental Microbiology 65: 3767–3773.

R. Khakhria, D. Duck and H. Lior, 1990, "Extended phage–typing scheme for *Escherichia coli* O157:H7", Epidemiol. Infect. 105: 511–520.

Antje Lorch, Sep. 1999, "Bacteriophages: An alternative to antibiotics?", Biotechnology and Development Monitor 39: 14–17.

J. Alisky, K. Iczkowski, A. Rapoport and N. Troitsky, 1998, "Bacteriophages show promise as antimicrobial agents", Journal of Infection 36: 5–15.

H. Williams Smith, Michael B. Huggins and Kathleen M. Shaw, 1987, "Factors influencing the survival and multiplication of bacteriophages in calves and their environment", Journal of General Microbiology 133: 1127–1135.

H. Williams Smith and M. B. Huggins, 1982, "Successful treatment of experimental *Escherichia coli* infections in mice using phage: its general superiority over antibiotics", Journal of General Microbiology 128: 307–318.

A. Reynaud, L. Cloastre, J. Bernard, H. Laveran, H.–W. Ackermann, D. Licois and B. Joly, 1992, "Characteristics and diffusion in the rabbit of a phage for *Escherichia coli* O103. Attempts to use this phage for therapy", Veterinary Microbiology 30: 203–212.

Carl R. Merril, Biswajit Biswas, Richard Carlton, Nicole C. Jensen, G. Joseph Creed, Steve Zullo and Sankar Adhya, Apr. 1996, "Long–circulating bacteriophage as antibacterial agents", Proceedings of the National Academy of Sciences USA 93: 3188–3192.

Paul Barrow, Margaret Lovell and Angelo Berchieri, Jr., Mar. 1998, "Use of lytic bacteriophage for control of experimental *Escherichia coli* septicemia and meningitis in chickens and calves", Clinical and Diagnostic Laboratory Immunology 5: 294–298.

H. Williams Smith and M. B. Huggins, 1983, "Effectiveness of phages in treating experimental *Escherichia coli* diarrhoea in calves, piglets and lambs", Journal of General Microbiology 129: 2659–2675.

H. Williams Smith, Michael B. Huggins and Kathleen M. Shaw, 1987, "The control of experimental *Escherichia coli* diarrhoea in calves by means of bacteriophages", Journal of General Microbiology 133: 1111–1126.

Alexander Sulakvelidze, Zemphira Alavidze and J. Glenn Morris Jr., Mar. 2001, "Bacteriophage Therapy", Antimicrobial Agents and Chemotherapy 45: 649–659.

*Primary Examiner*—Hankyel T. Park
(74) *Attorney, Agent, or Firm*—Michael R. Williams; Ryan W. Dupuis; Adrian D. Battison

(57) ABSTRACT

A method of reducing levels of *E. coli* O157 strains within the gastrointestinal tract of a ruminant animal using specific bacteriophage(s) is herein described. Also described is a pharmaceutical composition comprising at least one of said bacteriophages and a method for isolating or selecting bacteriophages useful in reducing *E. coli* O157 levels as described above.

12 Claims, No Drawings

USE OF BACTERIOPHAGES FOR CONTROL OF *ESCHERICHIA COLI* O157

This application claims priority under 35 USC §119(e) to Provisional Patent Application Ser. No. 60/209,608, filed Jun. 6, 2000.

FIELD OF THE INVENTION

The present invention relates generally to the field of molecular biology. More specifically, the present invention relates to the use of bacteriophages for reducing levels of *Escherichia coli* O157, and/or treating or preventing *Escherichia coli* O157 infection or diseases caused thereby, as well as methods for producing said bacteriophages.

BACKGROUND OF THE INVENTION

Human enteric infections with enterohemorrhagic *E. coli* O157 are a significant public health problem in many countries. They lead to diarrhea and to serious complications that include hemorrhagic colitis, the hemolytic uremic syndrome, thrombotic thrombocytopenic purpura, and death.

Healthy cattle carry *E. coli* O157 and humans acquire *E. coli* O157 infections most often by consuming food and water that has been contaminated with faeces from these animals. The demand for effective control of *E. coli* O157 infections at the pre-harvest level is high because it is generally believed that reducing, or eliminating *E. coli* O157 infections in cattle and other food animals will dramatically reduce the number of *E. coli* O157 infections in humans. Benefits occur not only through production of safer food, but through reduced transmission of *E. coli* O157 among cattle and dissemination in water and the environment. Probiotic bacteria, dietary management, and vaccination with relevant antigens could reduce shedding of *E. coli* O157 by cattle, however these approaches are poorly developed, or only marginally effective at this time.

Zhao et al. (*Journal of Clinical Microbiology* 36, 641–7, 1998; U.S. Pat. No. 5,965,128) showed that a mixture of probiotic bacteria, comprised of 18 isolates of *E. coli* and one *Proteus mirabilis* strain, reduced shedding of *E. coli* O157 by cattle. The mechanism by which the probiotic bacteria reduced the shedding of *E. coli* O157 is not known and the probiotic bacteria are not available commercially.

Hovde et al. (*Applied and Environmental Microbiology* 65, 3233–5, 1999) showed that higher energy, lower fiber diets reduced the duration of shedding of *E. coli* O157 by experimentally infected animals.

To date there are no reports of successful vaccination of cattle against carriage of *E. coli* O157.

Barrow et al. (Barrow et al., 1998, *Clin Diag Lab Imm* 5:294–298) demonstrated that bacteriophages can control septicemia and meningitis, both non-enteric infections, in a variety of animals. Both of these infections are systemic, rather than intestinal infections leading to diarrheal disease. The bacteriophages were not used to control *E. coli* O157, or other zoonotic enteric pathogens affecting humans.

Alisky et al. (Alisky et al., 1998, *J Infect* 36: 5–15) presented this recent review article that provides an historical perspective on the use of bacteriophages for controlling infections and current research in this area, which has been spurred by the emergence of antibiotic-resistant bacterial pathogens.

Bacteriophages have not been used to control *E. coli* O157 infections in cattle. Kudva et al. (*Applied and Environmental Microbiology* 65, 3767–73, 1999) recently reported that bacteriophages could kill *E. coli* O157 in pure culture, and speculated that bacteriophages could be used to control *E. coli* O157 in animals. However, the ability of phages to kill *E. coli* O157 in pure culture has been known for some time and forms the basis for a phage typing scheme for *E. coli* O157. It is of note that this in vitro effect of bacteriophages cannot be extended to therapeutic use in cattle without further research to establish that candidate bacteriophages survive in the bovine gastro-intestinal tract and retain the ability to infect and kill *E. coli* O157 in vivo. Moreover, bacteriophages for use in vivo must not adversely affect the health of treated animals.

Smith et al. (Smith et al., 1987, *J. Gen. Micro.* 133: 1111–1126) showed that experimental diarrhea in 6–12 hour old calves due to infection with certain enterotoxigenic strains of *E. coli* could be controlled by specific bacteriophages infecting those strains of bacteria. As will be appreciated by one knowledgeable of the art, serotypes of *E. coli* are defined by the presence of a combination of three known antigens on the surface of the cells and are a form of classification of different strains of *E. coli*. The antigens are O-antigens (somatic carbohydrate component of the cell wall lipopolysaccharide), H-antigens (flagella—organelles involved with cell locomotion), and K antigens (polysaccharide capsules or pili). The identity of these antigens on individual *E. coli* is determined by agglutination tests using specific, highly cross-adsorbed anti-sera. The O157:H7 serotype is one of many different known serotypes of *E. coli*. The strains used by Williams Smith are of different serotypes than O157:H7 (ie. different O, K, and H antigens). That is, these strains belong to the group of pathogens called enterotoxigenic *E. coli*, which cause disease by a mechanism distinct from that of *E. coli* O157. Furthermore, it is of note that the phages used by Williams Smith would not work on *E. coli* O157:H7 because it lacks the appropriate K antigen receptor. Furthermore, Williams Smith did not show that bacteriophages could be used to eliminate human zoonotic pathogens carried asymptomatically by cattle. It is also of note that the activity of the bacteriophages towards target organisms in host matrices and their stability in host matrices were not evaluated. Finally, the bacteriophages were not used to control *E. coli* O157, or other zoonotic enteric pathogens affecting humans.

U.S. Pat. Nos. 5,766,892 and 5,688,501 describe methods to treat bacterial infections in animals using bacteriophages that have been altered to resist host defense mechanisms. The bacteriophages were not used to control *E. coli* O157, or other zoonotic enteric pathogens affecting humans, but rather were serially administered to an animal's circulatory system and recovered so as to enrich for phage capable of surviving in the host circulatory system. Thus, these patents teach that phage must be modified to avoid the host immune system in order to be effective treatments.

SUMMARY OF THE INVENTION

According to a first aspect of the invention, there is provided a pharmaceutical composition comprising at least one bacteriophage selected from the group consisting y of: V4, V5, V5-re-isolated, V7, V8, V11 and V14.

According to a second aspect of the invention, there is provided a method of reducing levels of *E. coli* O157 in a ruminant animal comprising:

administering to a ruminant animal having *E. coli* O157 within its gastrointestinal tract at least one bacteriophage selected from the group consisting of: V4, V5, V5-re-isolated, V7, V8, V11, and V14; and retaining said ruminant animal under conditions such that said bacteriophage infect and lyse said *E. coli* O157, thereby reducing levels of *E. coli* O157 within the gastrointestinal tract of said ruminant animal.

According to a third aspect of the invention, there is provided a method of selecting and isolating bacteriophages capable of lysing *E. coli* O157 comprising:

administering to a ruminant animal having *E. coli* O157 within its gastrointestinal tract at least one bacteriophage selected from the group consisting of: V4, V5, V5-re-isolated, V7, V8, V11, and V14;

recovering gastrointestinal content from said ruminant animal;

isolating bacteriophage from said gastrointestinal content;

plating said isolated bacteriophage onto a suitable host; and purifying the resulting plaques.

According to a fourth aspect of the invention, there is provided a method of reducing levels of *E. coli* O157 in a matrix comprising:

administering to the matrix containing *E. coli* O157 therein at least one bacteriophage selected from the group consisting of: V4, V5, re-isolated V5, V7, V8, V11 and V14; and retaining said matrix under conditions such that said bacteriophage infect and lyse said *E. coli* O157, thereby reducing levels of *E. coli* O157 within the matrix.

According to a fifth aspect of the invention, there is provided a method of reducing the severity of, or preventing a disease caused by *E. coli* O157 comprising:

administering to an individual in need of such treatment a pharmaceutical composition comprising at least one bacteriophage selected from the group consisting of: V4, V5, V5-re-isolated, V7, V8, V11 and V14; and retaining said individual under conditions such that said bacteriophage infect and lyse said *E. coli* O157, thereby reducing levels of *E. coli* O157 within the gastrointestinal tract of said individual.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

As used herein, *E. coli* O157 refers to the prototype of the enterohemorrhagic *E. coli* (EHEC) which cause hemorrhagic colitis and the hemolytic uremic syndrome in humans, and includes EHEC O157:H7 and O157:H-.

As used herein, "matrix" or "matrices" refers to physical environments, for example but by no means limited to, physical environments that approximate the conditions in the gastrointestinal tract, in water or in manure.

As used herein, "gastrointestinal contents" comprises the four stomachs, small intestine and large intestine of a ruminant animal.

As used herein, "treated" refers to animals administered a pharmaceutical composition whereas "untreated" refers to control animals.

As used herein, "ruminant animal" refers to, for example, cattle, sheep, buffalo and goats, which convert plant material to food and fiber.

As used herein, "effective amount" refers to the administration of an amount of a given compound that achieves the desired effect.

As used herein, "bacteriophages V4, V5, V7, V8, V11 or V14" refers to bacteriophage phenotypically identical with bacteriophages V4, V5, V7, V8, V11, V14 respectively (Ahmed et al., 1987, *Journal of Infectious Diseases* 155:806–9). As will be well-known to one knowledgeable in the art, different isolates of a given bacteriophage may vary at the nucleic acid sequence level; however, these bacteriophage are considered to be identical provided they have similar phenotypes. As will be apparent to one knowledgeable in the art, different isolates may be prepared using means known in the art, for example, random chemical or ionizing radiation, recombinant DNA techniques, interbreeding and the like. It is of note that methods for phenotyping bacteriophage include, for example, determining host range.

As used herein, "bacteriophage V5-re-isolated" refers to a bacteriophage derived from V5 following growth in vivo in ruminant animal.

Enteric bacterial pathogens, such as *E. coli* O157:H7, are differentially sensitive to the bacteriophages that infect its species. This property has been exploited to develop useful bacteriophage-based schemes for sub-typing enteric bacteria for epidemiological purposes. However, this property makes the development of phage therapy for enteric pathogens difficult because ruminant animals may carry bacteriophage-resistant as well as sensitive strains of the pathogen that are capable of causing disease in humans.

To be used successfully to control human enteric pathogens in ruminant animals, bacteriophages must be capable of killing a broad spectrum of strains within the target species of pathogen and be effective in host matrices. Furthermore, the bacteriophages must survive in the ruminant gastrointestinal tract and retain the ability to infect and kill *E. coli* O157 in vivo. Moreover, bacteriophages for use in vivo must not adversely affect the health of treated animals. In this regard, rational selection of bacteriophages appropriate for phage therapy can be made based on information about the types of bacteria to be controlled, the reaction of potential bacteriophages with them, the activity of the bacteriophages against target organisms in host matrices, and the stability of the bacteriophages in the host matrices.

The invention involves a novel approach to control *E. coli* O157 in ruminant animals. It involves oral administration of bacteriophages lytic to *E. coli* O157 to ruminant animals to reduce or eliminate *E. coli* O157 in their gastrointestinal tract. It also involves a process for selecting lytic bacteriophages suitable for this purpose.

In other embodiments, a pharmaceutical composition comprising at least one of the bacteriophages is prepared. As will be appreciated by one knowledgeable in the art, the pharmaceutical composition may be used to treat or prevent *E. coli* O157 infections in mammals in need of such treatment, for example, humans. In addition, at least one bacteriophage may be used to reduce levels of or eliminate *E. coli* O157 in matrices, for example, well water, municipal water, ground water, manure, foods, produce, and the like.

In one embodiment of the invention, there is provided a method for reducing levels of *E. coli* O157 in ruminant animals by oral administration of a pharmaceutical composition comprising at least one bacteriophage selected from the group consisting of bacteriophages V4, V5, V7, V8, V11, V14 (Ahmed et al., 1987, *Journal of Infectious Diseases* 155:806–9) and combinations thereof to ruminant animals. These bacteriophage have previously been used in phage-typing to identify strains of *E. coli* O157 in vitro but have not been used to reduce levels of *E. coli* O157 in ruminant animals. As discussed above, the ability of bacteriophage to kill *E. coli* strains in vitro does not guarantee their effectiveness in vivo.

For use, the pharmaceutical composition comprising at least one of bacteriophages V4, V5, V5-re-isolated, V7, V8, V11 or V14 is prepared as described below. The pharmaceutical composition is then administered to a bovine animal having *E. coli* O157 within its gastrointestinal tract. As discussed below, administration of the bacteriophage(s) results in decreased levels of fecal shedding immediately following challenge ($p<0.05$) and eliminates the organism from treated but not untreated cattle after 8 days following challenge. Thus, the pharmaceutical composition enters the digestive tract of the cow and lyses the *E. coli* O157, thereby reducing levels of the organism within the host and eliminating shedding of the bacteria by the host. As will be apparent to one knowledgeable in the art, elimination of the bacteria eliminates the risk of contamination of food and other products (and ultimately humans) with *E. coli* O157. In other embodiments, the pharmaceutical composition is used as a prophylactic for preventing development of disease symptoms or lessening severity of symptoms in individiuals suspected of contracting *E. coli* O157 infection.

As discussed above, infection of humans with *E. coli* O157 may lead to diarrhea and serious complications that include hemorrhagic colitis, the hemolytic uremic syndrome, thrombotic thrombocytopenic purpura, and death. Specifically, the bacteria produce a toxin and other factors which causes damage to the lining of the intestine and blood vessels in other organs. The symptoms associated with *E. coli* O157 infection include severe cramping, diarrhea and vomiting. Thus, administering the pharmaceutical composition comprising at least one of bacteriophages V4, V5, V7, V8, V11 or V14 will reduce the level of *E. coli* O157 in the gastrointestinal tract of an individual in need of such a treatment by lysing the bacteria. This in turn will reduce the severity of symptoms associated with *E. coli* O157 infection in said individual.

In other embodiments, at least one of bacteriophages V4, V5, V5-re-isolated, V7, V8, V11 or V14 is administered to a matrix, for example, a water supply or a manure pile, to reduce the levels of *E. coli* O157 in said matrix. As will be appreciated by one knowledgeable in the art, reducing the levels of *E. coli* O157 in the matrix will in turn reduce the chance of subsequent contamination or infection.

The preferred delivery vehicles for the bacteriophages are in aqueous suspension, in a tablet or capsule form, as a powder or coating, or incorporated on or in material that can be eaten. However, as will be appreciated by one knowledgeable in the art, any suitable preparation which allows delivery of the bacteriophage into the gastrointestinal tract of the animal is within the scope of the invention. For examples of suitable carriers, diluents, excipients and the like, see *Remington: The Science and Practice of Pharmacy*, 2000, Gennaro, AR ed., Eaton, Pa. Mack Publishing Co.

In some embodiments, the pharmaceutical composition comprises bacteriophage at a titer of approximately $10^2$–$10^{10}$ PFU/ml or PFU/g. In other embodiments, the titer may be $10^5$–$10^9$ PFU/ml or PFU/g. As will be apparent to one knowledgeable of the art, the titer used may vary according to, for example, the animal or individual being treated, the degree of infection and the state of disease progression.

In another aspect of the invention, there is provided a method of enriching for or selecting bacteriophage capable of lysing *E. coli* O157 under specific conditions. Specifically, a host carrying *E. coli* O157 in its gastrointestinal tract is fed a pharmaceutical composition as described above. In some embodiments, the pharmaceutical composition comprises at least one of V4, V5, V5-re-isolated, V7, V8, V11, V14 or preferably mixtures thereof. Gastrointestinal contents from the host are recovered over time and are filtered to recover bacteriophage. The filtrate is then plated onto host bacterial cells, for example, suitable strains of *E. coli* O157 and grown under conditions such that plaques form. As will be apparent to one knowledgeable of the art, the plaques contain the desired bacteriophage. Yet another aspect of the invention is directed to bacteriophage or mixtures of bacteriophages isolated by this method and the use thereof to reduce *E. coli* O157 levels in ruminant animals.

In other embodiments, the bacteriophage are used in combination with other treatments known in the art for reducing levels of or treating infection by *E. coli* O157, for example, antibiotics, antibodies and the like.

EXAMPLE 1
Screening Bacteriophages Based on Ability to React with Different *E. coli* O157:H7

Greater than 98% of *E. coli* O157:H7 are susceptible to lysis by one or more of the 14 lytic bacteriophages that are used to type the pathogen (Khakhria et al., 1990). Based on the frequency with which the different phage types are encountered (Khakhria et al., 1990) (Table 1) and knowledge about susceptibility of the phage types to the lytic phage typing bacteriophages (Khakhria et al., 1990), it was predicted that a mixture of bacteriophages V4, V5, V7, V8, V11, and V14 is active against greater than 98% of *E. coli* O157:H7.

EXAMPLE 2
Screening of Bacteriophages for Ability to Kill *E. coli* O157:H7 in Matrices Encountered in Cattle Selection of bacteriophages appropriate for phage therapy can be made based on detailed information about their ability to kill *E. coli* O157:H7 in host matrices. Such information can be gained from experiments performed in vitro, as described below.

Eleven virulent bacteriophages from the group of bacteriophages used to type *E. coli* O157:H7 (V1, V2, V4, V5, V7, V8, V11, V12, V14, V15, and V14) were evaluated as potential agents for phage therapy of *E. coli* O157:H7 infections in cattle. The suitability of the bacteriophages for phage therapy was evaluated by testing their ability to reduce the numbers of *E. coli* O157:H7 in feces and rumen fluid. One ml of rumen fluid or feces (diluted 1:3 (v/v) with 0.9% saline) containing approximately $10^3$ colony forming units (CFU) of *E. coli* O157:H7 strain R508 (which is sensitive to all the typing bacteriophages and resistant to nalidixic acid) was treated with 0, $2\times10^5$, $2\times10^6$, $1\times10^8$ plaque forming units (PFU) of bacteriophage for 24 hours at 37° C., 22° C., and 10° C. after which dilutions of the mixtures were plated on MacConkey Agar containing nalidixic acid to determine the number of bacteria in each sample. Samples of each matrix containing no added bacteria or bacteria in the absence of phage were included as controls. As can be seen in Table 2, bacteriophages V4, V5, V7, V8, V11, and V14 are most active against *E. coli* O157:H7 in bovine feces at 37° C. Bacteriophage V4 is active against *E. coli* O157:H7 in feces at all temperatures tested. Bacteriophages V5 and V7, are active against *E. coli* O157:H7 in rumen fluid at 10° C. and V7, is active in rumen fluid at 37° C.

EXAMPLE 3
Screening of Bacteriophages for Stability in Matrices Encountered in Cattle The stability of bacteriophages V1, V2, V4, V5, V7, V8, V11, V12, V14 and V16 in feces and rumen fluid was evaluated as follows. Zero or approximately $10^6$ PFU were added to 1 ml of rumen fluid or feces (diluted 1:3 (v/v) with 0.9% saline) and the mixture was incubated at 37° C. After 5 and 24 h the mixture was centrifuged for 5 min to remove particulate matter then the supernatant was filtered through a 0.2 $\mu$m filter. The number of infective phage particles remaining in each filtrate was determined by titration on *E. coli* O157:H7 strain R508. 90 μl of serial 1:9 (v/v) dilutions of phage in Lambda Diluent were incubated with 10 μl of late log phase bacterial culture *E. coli* O157:H7 strain R508 for 20 min at 37° C., then 20 μl of each mixture was dropped onto the surface of a Modified Nutrient Agar plate. After the drops were absorbed into the agar, the plate was inverted and incubated overnight at 37° C. and observed for the presence of plaques. Samples of each matrix containing no added phage were included to ensure each matrix did not contain phage capable of infecting the host strain used to titrate the samples. A phage was considered stable in a matrix if 10% or more of the added phage remained following incubation in the matrix.

In general, all the bacteriophages were stable in feces for 5 hours at 37° C. (Table 3), however V7, and V11 were unstable in feces after 24 hours incubation at this temperature. Only V4, V5, V8 and V14 were stable in rumen fluid for 24 hours (Table 3).

EXAMPLE 4
Rational Selection of Bacteriophages for Phage Therapy to Control *E. coli* O157:H7 Infections in Cattle Consideration of the susceptibility of different strains of *E. coli* O157:H7 to the bacteriophages (Example 1), activity of the bacteriophages against *E. coli* O157:H7 in rumen fluid and feces (Example 2), and stability of the bacteriophages in rumen fluid and feces (Example 3), indicated that bacteriophages V4, V5, V7, V8, V11, and V14 are most suitable for use in phage therapy. Individually, the bacteriophages active against *E. coli* O157:H7 in rumen fluid and feces, are stable in these matrices and together they are expected to be effective against more than 98% of *E. coli* O157:H7 strains.

EXAMPLE 5
Phage Therapy Controls *E. coli* O157:H7 Infection in Cattle

A mixture of $10^{11}$ PFU of bacteriophages V4, V5, V7, V8, V11, and V14 was administered orally to five calves in milk replacer containing 10% calcium bicarbonate four times before and once after oral challenge with $3 \times 10^9$ CFU of *E. coli* O157:H7 strain E318N in 500 ml of milk replacer. *E. coli* O157:H7 strain E318N is a phage type 4 strain that is resistant to nalidixic acid, which permits its enumeration in feces by plating on selective agar. Five calves that received bacteriophages only and five calves that received *E. coli* O157:H7 only served as control groups for this experiment. Feces from cattle in all groups were collected over 16 days after oral challenge with *E. coli* O157:H7, and tested for the presence of *E. coli* O157:H7 and bacteriophage.

*Escherichia coli* O157:H7 strain E318N was enumerated by direct plating of decimal dilutions of feces in duplicate onto sorbitol MacConkey agar containing nalidixic acid (SMAC-NAL). After overnight incubation at 42° C., sorbitol-negative colonies were subcultured and subjected to agglutination with anti-O157 serum to confirm their identity as the challenge strain. The theoretical limit of detection of *E. coli* O157:H7 using the direct plating method was 50 CFU/g. Fecal samples that were negative by the direct plating method were enriched in modified Trypticase Soy Broth containing vancomycin and cefsulodin for 6 h at 42° C. *Escherichia coli* O157:H7 in the culture was detected by immunomagnetic separation using Dynal O157 beads followed by plating on SMAC-NAL, as described above. The theoretical limit of detection of *E. coli* O157:H7 using the enrichment method was 1 CFU/g.

*Escherichia coli* O157:H7 bacteriophage were enumerated according to the method of Smith and Huggins (Smith and Huggins, 1983, *J Gen Micro* 129:2659–2675), with modifications. Briefly, *E. coli* O157:H7 strain R508 (which is sensitive to all the bacteriophages used in the phage therapy mixture) was infected with serial dilutions of sterile fecal filtrates for 20 minutes at 37° C., then duplicate aliquots of the mixture were spread onto the surface of Modified Nutrient Agar plates. The plates were examined visually for the presence of plaques after overnight incubation at 37° C. The theoretical limit of detection of bacteriophages using this method was 50 PFU/g. All the calves that received *E. coli* O157:H7 strain E318N shed detectable numbers of challenge organism in their feces (Table 4). The calves that did not receive *E. coli* O157:H7 strain E318N did not shed the challenge organism. The mean duration of shedding of *E. coli* O157:H7 E318N by the calves that received the challenge organism only was 14±4.2 days and 7.6±1.7 days by the calves that received bacteriophages and the challenge organism. Phage therapy reduced the duration of shedding of *E. coli* O157 by cattle ($p<0.05$). It also reduced the number of *E. coli* O157:H7 shed in feces on day 2 and day 4 ($p<0.05$).

All the calves that received bacteriophages orally shed detectable numbers of bacteriophages in their feces (Table 5). Calves that did not receive bacteriophages did not shed bacteriophages (not shown). The mean duration of shedding of bacteriophages following the final administration of bacteriophages was 3±1.4 days by the group that received bacteriophages only and 9±2.4 days by the calves that received bacteriophages and *E. coli* O157:H7. The calves in the group that received bacteriophages only cleared the bacteriophages more rapidly than the calves in the group that received bacteriophages and *E. coli* O157:H7 ($p<0.05$). In both groups of calves there was an initial decline in the number of bacteriophages shed in the feces, and there was no significant difference in the number of bacteriophages shed in feces on day 2. In the group that received bacteriophages and *E. coli* O157:H7 there was a rapid increase in the numbers bacteriophages shed by all calves. This rise to $10^7$–$10^{10}$ PFU/g feces coincided with time that *E. coli* O157:H7 E318N in the feces fell to undetectable levels (Table 4, 5).

EXAMPLE 6
Enrichment and Selection of Bacteriophage Capable of Lysing *E. coli* Under Specific Conditions Bacteriophage capable of lysing *E. coli* O157 in the gastrointestinal tract of ruminants were enriched and selected as follows. Bacteriophages from calves infected with *E. coli* O157:H7 strain E318N and treated with a mixture of $10^{11}$ PFU of V4, V5, V7, V8, V11, and V14 described in example 5, above, were isolated and purified from day 8 fecal samples using methods know to those skilled in the art. As will be apparent to one knowledgeable in the art, other gastrointestinal contents may be used in places of feces. Fecal samples taken on day 8 from treated calves were used because they contained high numbers of phage and the fecal samples from control calves contained undetectable numbers of phage. Fifty phage were isolated from day 8 feces from the treated group. Ten of these were shown to be derived from V5 or V7, by restriction endonuclease mapping of phage genomic DNA. These and the other 40 phage isolates exhibited virulence pattern identical to pattern of activity of V5 towards bacteria belonging to O157 phage types PT2, PT23, PT67, and PT14, indicating that they were derivatives of V5 rather than V7. The phages were designated V5 re-isolated or re-isolated V5.

As will be apparent to one knowledgeable in the art, mutations can be provoked in bacteriophage while grown in host bacteria. These phage can then be passed through the above described enrichment and selection method to isolate bacteriophage.

While the preferred embodiments of the invention have been described above, it will be recognized and understood that various modifications may be made therein, and the appended claims are intended to cover all such modifications which may fall within the spirit and scope of the invention.

TABLE 1

Sensitivity of E. coli O157:H7 to bacteriophage V4, V5, V7, V11, and V14.

| Phage Type[a] | Percentage of Total Isolates Typed[b] | Bacteriophage Sensitivity[c] | | | | | | Proportion of Active Phages |
|---|---|---|---|---|---|---|---|---|
| | | V4 | V5 | V7 | V8 | V11 | V14 | |
| 14 | 49.8 | +[d] | + | + | + | + | + | 6/6 |
| 2 | 10.0 | + | −[e] | + | + | + | − | 4/6 |
| 31 | 9.4 | − | − | − | − | + | − | 1/6 |
| 1 | 5.2 | + | + | + | + | + | + | 6/6 |
| 4 | 4.6 | + | + | + | + | + | + | 6/6 |
| 8 | 3.5 | + | + | + | + | + | + | 6/6 |
| 10 | 3.3 | + | + | − | + | + | + | 5/6 |
| 32 | 2.5 | − | − | + | − | + | − | 2/6 |
| atypical | 1.9 | ±[f] | ± | ± | ± | ± | ± | na[g] |
| 49 | 1.7 | + | + | + | + | + | + | 6/6 |
| 23 | 1.5 | − | − | + | + | + | − | 3/6 |
| 21 | 1.2 | − | − | + | − | − | − | 1/6 |
| 64 | 1.0 | + | + | + | − | − | + | 4/6 |
| 33 | 0.8 | − | − | + | − | + | − | 2/6 |
| 81 | 0.6 | − | − | − | + | + | − | 2/6 |
| 39 | 0.4 | − | − | + | + | + | − | 3/6 |
| 40 | 0.4 | − | − | + | + | + | − | 3/6 |
| 53 | 0.4 | + | + | + | + | + | − | 5/6 |
| 61 | 0.4 | + | + | + | + | + | + | 6/6 |
| 70 | 0.4 | − | − | + | + | + | − | 3/6 |
| 41 | 0.2 | + | + | + | + | + | + | 6/6 |
| 50 | 0.2 | − | − | + | + | + | − | 3/6 |
| 54 | 0.2 | − | − | + | + | + | − | 3/6 |

[a]Khakhria et al. (1990).
[b]Enteric Pathogens Identified in Canada During the Year 1995, Annual Summary. Khakhria et al. (1997). National Laboratory for Enteric Pathogens.
[c]as noted by Khakhria et al. (1990).
[d]strains reacts with the bacteriophage at the routine test dilution.
[e]strains do not react with the bacteriophage at the routine test dilution.
[f]strain may or may not react with the bacteriophage at the routine test dilution; no definitive phage type assigned.
[g]not applicable.

TABLE 2

Bacteriophages active against E. coli O157:H7 in feces and rumen fluid at different temperatures.

| Matrix | Temperature | Active Bacteriophages[a] |
|---|---|---|
| Feces | 37° C. | V4, V5, V7, V8, V11, V14 |
| | 22° C. | V2, V4, V5, V8, V16 |
| | 10° C. | V4 |
| Rumen Fluid | 37° C. | V7 |
| | 22° C. | none |
| | 10° C. | V5, V8 |

[a]the bacteriophage was deemed active if it reduced the number of viable target organisms in the matrix by at least 90% compared to the non-bacteriophage treated sample

TABLE 3

Stability of bacteriophages in feces and rumen fluid at different temperatures.

| Bacteriophage | Feces | | Rumen Fluid | |
|---|---|---|---|---|
| | 5 hours | 24 hours | 5 hours | 24 hours |
| V1 | +[a] | + | −[b] | − |
| V2 | + | + | − | − |
| V4 | + | + | + | + |
| V5 | + | + | + | + |
| V7 | + | − | + | − |
| V8 | + | + | + | + |
| V11 | + | − | + | − |
| V12 | + | + | + | − |
| V14 | + | + | + | + |
| V16 | + | + | + | − |

[a]>10% of phage remaining after incubation period;
[b]<less than 10% of phage remaining after incubation period

TABLE 4

Detection of E. coli O157:H7 in feces of calves administered phages + E. coli O157:H7 and E. coli O157:H7 alone.

| Days after challenge with E. coli O157:H7 | Log₁₀(CFU/gram feces) | | | | | | | | | |
|---|---|---|---|---|---|---|---|---|---|---|
| | Phages + E. coli O157:H7 group[a] | | | | | E. coli O157:H7 alone group[b] | | | | |
| | Calf 6 | Calf 7 | Calf 8 | Calf 9 | Calf 10 | Calf 11 | Calf 12 | Calf 13 | Calf 14 | Calf 15 |
| 2 | 3.16 | 3.66 | 3.00 | 3.30 | 3.35 | 3.17 | 4.14 | 4.92 | 5.48 | 4.65 |
| 4 | 2.70 | 3.80 | 2.79 | +[c] | + | 2.85 | 3.95 | 5.13 | 5.20 | 4.22 |
| 6 | 4.98 | 2.88 | + | − | + | + | + | 3.89 | 3.95 | 2.94 |
| 8 | − | − | 2.48 | + | − | + | − | + | 2.30 | + |
| 10 | − | − | − | − | − | 1.40 | − | + | + | 2.70 |
| 12 | − | − | − | − | − | 2.60 | − | − | 2.08 | + |

TABLE 4-continued

Detection of *E. coli* O157:H7 in feces of calves administered phages + *E. coli* O157:H7 and *E. coli* O157:H7 alone.

| Days after challenge with *E. coli* O157:H7 | Log$_{10}$(CFU/gram feces) | | | | | | | | | |
|---|---|---|---|---|---|---|---|---|---|---|
| | Phages + *E. coli* O157:H7 group[a] | | | | | *E. coli* O157:H7 alone group[b] | | | | |
| | Calf 6 | Calf 7 | Calf 8 | Calf 9 | Calf 10 | Calf 11 | Calf 12 | Calf 13 | Calf 14 | Calf 15 |
| 14 | – | – | – | – | – | – | – | – | – | + |
| 16 | – | – | – | – | – | 3.78 | – | – | – | + |

[a]calves in this group received 10$^{11}$ PFU of phages V4, V5, V7, V8, V11, and V14 on days –7, –6, –1, 0, and 1.
[a]calves in this group received 10$^{11}$ PFU of phages V4, V5, V7, V8, V11, and V14 on days –7, –6, –1, 0 and 1 and 3 × 10$^5$ CFU of *E. coli* O157:H7 E318N 4b after administration of the phages on day 0.
[b]calves in this group received 3 × 10$^5$ CFU of *E. coli* O157:H7 E318N on day 0.
[d]<50 CFU/g by direct plating or <1 CFU/g by selective enrichment followed by immunomagentic separation. Selective enrichment followed by immunomagnetic separation was used if direct plating of feces from phages + *E. coli* O157:H7 and *E. coli* O157:h7 groups were negative.
[c]positive by selective enrichment followed by immunomagnetic separation; feces contained ≧1, but <50 CFU/g.

TABLE 5

Detection of phages infecting *E. coli* O157:H7 in feces of calves administered phages alone and phages + *E. coli* O157:H7.

| Days after challenge with *E. coli* O157:H7 | Log$_{10}$(PFU/gram feces) | | | | | | | | | |
|---|---|---|---|---|---|---|---|---|---|---|
| | Phages alone group[a] | | | | | Phages + *E. coli* O157:H7 group[b] | | | | |
| | Calf 1 | Calf 2 | Calf 3 | Calf 4 | Calf 5 | Calf 6 | Calf 7 | Calf 8 | Calf 9 | Calf 10 |
| 2 | 4.87 | 6.15 | 4.53 | 3.40 | 4.30 | 4.92 | 3.83 | 3.87 | 4.39 | 3.42 |
| 4 | 2.40 | 2.51 | –[d] | – | 2.30 | 3.02 | 3.23 | 3.02 | 2.88 | 2.00 |
| 6 | – | – | – | 2.44 | – | – | 2.75 | 7.53 | 7.70 | 3.80 |
| 8 | – | – | – | – | – | 7.63 | 8.15 | 6.68 | 7.95 | 8.77 |
| 10 | – | – | – | – | – | 10.21 | 5.82 | 3.90 | – | – |
| 12 | – | – | – | – | – | 7.28 | – | – | – | – |
| 14 | – | – | – | – | – | 6.81 | – | – | – | – |
| 16 | – | – | – | – | – | – | – | 2.40 | – | – |

[a]calves in this group received 10$^{11}$ PFU of phages V4, V5, V7, V8, V11, and V14 on days –7, –6, –1, 0, and 1.
[b]calves in this group received 10$^{11}$ PFU of phages V4, V5, V7, V8, V11, and V14 on days –7, –6, –1, 0 and 1 and 3 × 10$^5$ CFU of *E. coli* O157:H7 E318N 4h after administration of the phages on day 0.
[c]calves in this group received 3 × 10$^5$ CFU of *E. coli* O157:H7 E318N on day 0.
[d]<50 PFU/g feces.

What is claimed is:

1. A pharmaceutical composition comprising at least one bacteriophage selected from the group consisting of: V4, V5, V5-re-isolated; V7, V8, V11 and V14.

2. The pharmaceutical composition according to claim 1 wherein the bacteriophage is V5.

3. The pharmaceutical composition according to claim 1 wherein the bacteriophage is re-isolated V5.

4. A method of reducing levels of *E. coli* O157 in a ruminant animal comprising:
    administering to a ruminant animal having *E. coli* O157 within its gastrointestinal tract at least one bacteriophage selected from the group consisting of: V4, V5, re-isolated V5, V7, V8, V11, and V14; and
    retaining said ruminant animal under conditions such that said bacteriophage infect and lyse said *E. coli* O157, thereby reducing levels of *E. coli* O157 within the gastrointestinal tract of said ruminant animal.

5. The method according to claim 4 wherein the bacteriophage is V5.

6. The method according to claim 4 wherein the bacteriophage is re-isolated V5.

7. The method according to claim 4 wherein the ruminant animal is a bovine animal.

8. A method of selecting and isolating bacteriophages capable of lysing *E. coli* O157 comprising:
    administering to a ruminant animal having *E. coli* O157 within its gastrointestinal tract at least one bacteriophage selected from the group consisting of: V4, V5, V7, V8, V11, and V14;
    recovering gastrointestinal content from said ruminant animal;
    isolating bacteriophage from said gastrointestinal content;
    plating said isolated bacteriophage onto a suitable host; and
    purifying the resulting plaques.

9. Bacteriophages isolated according to the method of claim 8.

10. A method of reducing levels of *E. coli* O157 in a matrix comprising:
    administering to the matrix containing *E. coli* O157 therein at least one bacteriophage selected from the group consisting of: V4, V5, re-isolated V5, V7, V8, V11 and V14; and retaining said matrix under conditions such that said bacteriophage infect and lyse said *E. coli* O157, thereby reducing levels of *E. coli* O157 within the matrix.

11. The method according to claim 10 wherein the matrix is manure.

12. A method of preventing or reducing the severity of disease caused by *E. coli* O157 comprising:

administering to an individual in need of such treatment a pharmaceutical composition comprising at least one bacteriophage selected from the group consisting of: V4, V5, re-isolated V5, V7, V8, V11 and V14; and retaining said individual under conditions such that said bacteriophage infect and lyse said *E. coli* O157, thereby reducing levels of *E. coli* O157 within the gastrointestinal tract of said individual.

* * * * *